US011020594B2

(12) United States Patent
Chen et al.

(10) Patent No.: US 11,020,594 B2
(45) Date of Patent: Jun. 1, 2021

(54) ELECTROCHEMICAL DEPHOSPHORYLATION TECHNIQUE FOR TREATING ALZHEIMER'S DISEASE AND USE THEREOF

(71) Applicant: NATIONAL CHIAO TUNG UNIVERSITY, Hsinchu (TW)

(72) Inventors: Jung-Chih Chen, Hsinchu (TW); I-Chiu Li, Hsinchu (TW); Kun-Che Li, Hsinchu (TW); Ching-Cheng Chuang, Hsinchu (TW); Mei-Lan Ko, Hsinchu (TW); Hsin-Yu Chen, Hsinchu (TW); Chia-Hsuan Chang, Hsinchu (TW); Hsin-Yi Tsai, Hsinchu (TW); Chien-Chih Hsu, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 16/441,632

(22) Filed: Jun. 14, 2019

(65) Prior Publication Data
US 2020/0391033 A1    Dec. 17, 2020

(51) Int. Cl.
*A61N 1/36* (2006.01)
*A61N 1/05* (2006.01)

(52) U.S. Cl.
CPC ....... *A61N 1/36082* (2013.01); *A61N 1/0536* (2013.01)

(58) Field of Classification Search
CPC .... A61N 1/36082; A61N 1/0536; A61N 1/04; A61N 1/0408
See application file for complete search history.

(56) References Cited

U.S. PATENT DOCUMENTS

| | | | |
|---|---|---|---|
| 2013/0123600 A1* | 5/2013 | Tcheng | A61B 5/4839 600/378 |
| 2013/0177836 A1* | 7/2013 | Janata | H01M 4/9008 429/506 |
| 2015/0064604 A1* | 3/2015 | Jonke | H01M 4/8853 429/506 |
| 2016/0067526 A1 | 3/2016 | Yang | |
| 2020/0338358 A1* | 10/2020 | Makansi | A61N 1/37514 |
| 2020/0393438 A1* | 12/2020 | Wijdenes | G01N 33/4836 |

* cited by examiner

*Primary Examiner* — Christopher Koharski
*Assistant Examiner* — James Moss
(74) *Attorney, Agent, or Firm* — Rosenberg, Klein & Lee (57) ABSTRACT

The invention relates to an electrochemical dephosphorylation technique for treating Alzheimer's disease and a use thereof. It comprises a gold electrode provided with a negative potential of −0.2 V to −0.6 V on a surface thereof.

1 Claim, 9 Drawing Sheets

| PANI | PANI containing phosphoric acid | PANI dephosphorylation |

Tau proteins deposited for 4 hrs

Tau proteins deposited for 24 hrs

FIG. 7

PANI phosphorylation

FIG. 8

PANI dephosphorylation

FIG. 9

ELECTROCHEMICAL DEPHOSPHORYLATION TECHNIQUE FOR TREATING ALZHEIMER'S DISEASE AND USE THEREOF

BACKGROUND OF THE INVENTION

1. Field of the Invention

The present invention relates to an electrochemical dephosphorylation technique for treating Alzheimer's disease and use thereof which dephosphorylates Tau proteins in a specific brain region by an electrode to treat Alzheimer's disease.

2. Description of Related Art

Pathological studies have shown that there are two main causes of the gradual death of brain neurons in patients with Alzheimer's disease (AD). One of the main causes is the production of insoluble β-amyloid plaques (Aβ) by cells surrounding the cerebral cortex. The other main cause includes excessive phosphorylation of Tau proteins in brain cells, resulting in accumulation of paired helical filaments, and abnormal aggregation of Tau proteins to produce neurofibrillary tangles (NFTs). Thus, the delivery system of the neuron is disrupted and the level of neurotransmitter such as acetylcholine is reduced, resulting in structural lesions of the nerve cells and the death of peripheral nerve cells in brain.

At present, most treatments for Alzheimer's disease have not yet appeared to effectively cure or reverse the progression of the disease, and only a few can be temporarily used to relieve the symptoms. Furthermore, the blood vessels in the brain have a blood-brain barrier, so more than 98% of the therapeutic drugs can't pass through the blood-brain barrier to enter the brain. Delivering the therapeutic drugs to the brain remains a challenging task to treat central nervous system disease.

In order to improve the efficiency of drug treatment, the methods of using focused ultrasound (FUS) to stimulate the blood-brain barrier with microbubbles have been developed in recent years. By the resonance characteristics of microbubbles, cavitation is generated under the stimulation of focused ultrasound to temporarily open the blood-brain barrier, thereby improving the efficiency of drug delivery.

Additionally, scanning ultrasound technology can be used to treat Alzheimer's disease in mice by use of 0.7-MPa peak rarefactional pressure, 10-Hz pulse repetition frequency, 10% duty cycle, 1 MHz center frequency, and 6-s sonication time per spot to open the blood-brain barrier, and restore memory by breaking apart the neurotoxic Amyloid-β plaques without additional therapeutic drugs (Science Translational Medicine, (2015), 7(278): 278ra33).

The U.S. Pat. Pub. No. US20160067526A1, published on 10 Mar. 2016, has disclosed a method for treating and/or preventing neurodegenerative diseases by applying low-intensity pulsed ultrasound. A low-intensity pulsed ultrasound apparatus used in the method comprises a focused piezoelectric transducer, a power amplifier, a function generator connected to the power amplifier and a power sensor module. The apparatus produces low-intensity pulsed ultrasound after being worn in the head of a patient with a neurodegenerative disease, increases the expression level of glial cell line-derived neurotrophic factor (GDNF) mediated by integrin and slows down the memory impairment induced by aluminum chloride.

However, the safety and efficacy of the above methods in clinical application still have to be evaluated. Therefore, it is necessary to continuously develop various methods for treating Alzheimer's disease.

SUMMARY OF THE INVENTION

The object of the present invention is to provide an electrochemical dephosphorylation technique for treating Alzheimer's disease and use thereof which comprises a gold electrode provided with a negative potential of dephosphorylated function on a surface thereof for electrically stimulating a specific brain region so as to achieve the purpose of dephosphorylation of the phosphorylated Tau proteins.

Disclosed herein is an electrochemical dephosphorylation electrode for treating Alzheimer's disease. It comprises a gold electrode provided with a negative potential of −0.2 V to −0.6 V on a surface thereof. Preferably, the gold electrode is deposited like a plane.

A method for treating Alzheimer's disease by use of the electrochemical dephosphorylation electrode is also disclosed herein. It comprises the steps of applying the electrochemical dephosphorylation electrode to a hippocampus region having neurofibrillary tangles and neuritic plaques to dephosphorylate Tau proteins of an individual in need.

DETAILED DESCRIPTION OF THE PREFERRED EMBODIMENT

The present invention relates to an electrochemical dephosphorylation electrode for treating Alzheimer's disease and a method for treating Alzheimer's disease by use of the electrochemical dephosphorylation electrode.

The method comprises the steps of applying an electrochemical dephosphorylation electrode to a hippocampus region having neurofibrillary tangles and neuritic plaques to dephosphorylate Tau proteins of an individual in need. The electrochemical dephosphorylation electrode comprises a gold electrode provided with a negative potential of −0.2 V to −0.6 V on a surface thereof.

Hereinafter, an exemplary embodiment of the present invention will be described in detail with reference to the accompanying drawings.

Example 1

1. Preparation of Gold Electrode

A crystal oscillator (Frequency oscillator, Model: CHI-405C) (Crystal, CH instruments, USA, Catalog: 151215) was used in this example. The fundamental frequency of the quartz crystal was 7.995 MHz. Both sides of the quartz crystal were respectively provided with a gold thin film which was deposited on a top of the crystal as a working electrode.

2. Preparation of Polyaniline (PANI) Film for Testing the Gold Electrode

Figure 1:
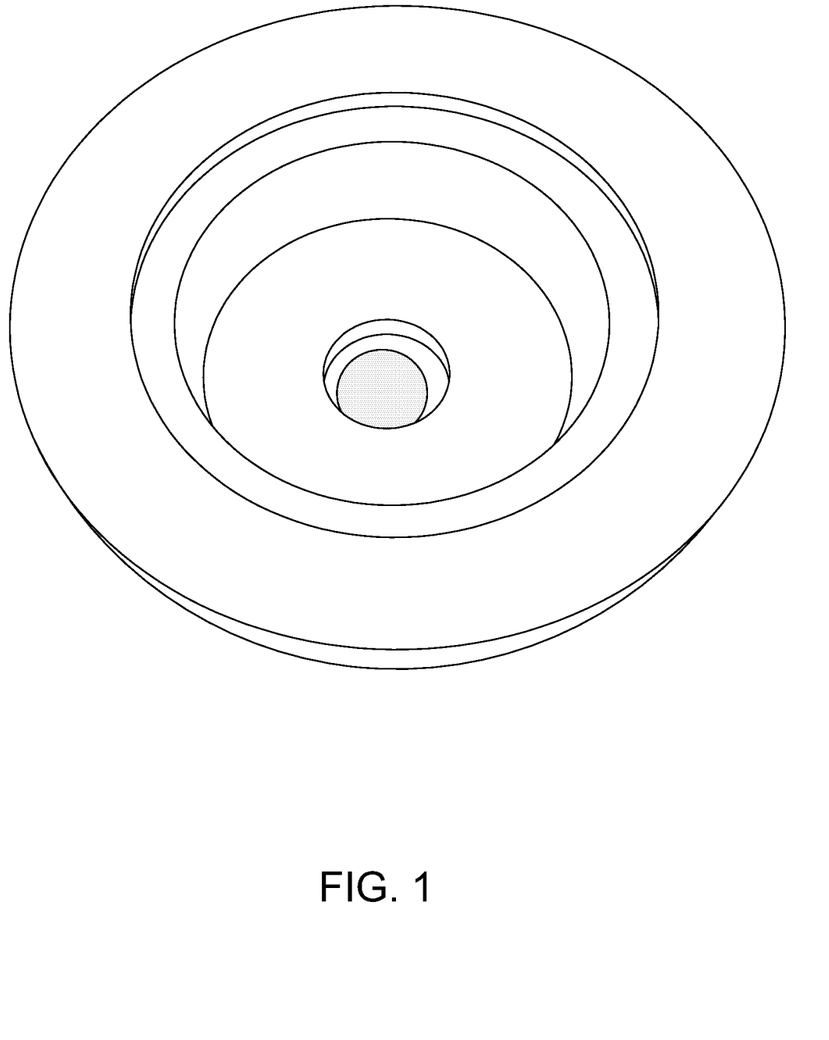
FIG. 1 is a schematic diagram showing a polyaniline (PANI) film according to the present invention.

An electrochemical quartz crystal microbalance (EQCM) (CH instruments, USA, model CHI-405C) was used in this example to detect the effect of a gold electrode. A polyaniline (PANI) film was prepared by a potentiostatic method and modified on the gold electrode to serve as a dephosphorylated carrier, and its electrochemical properties were tested. When preparing the PANI film, the most suitable parameters were acquired by the potentiostatic method. The amount of charge was converted according to the change of current with time, and the mass and thickness of the PANI film were converted by the frequency variation. Since the PANI film has a positive charge, the phosphates were adsorbed on the positively charged PANI film after phosphoric acids were added. Then, the change of the negative potential was used to test whether the phosphates were detached from the PANI film, and the phosphate elimination rate was instantaneously converted by the frequency variation. In preparing the PANI film by the potentiostatic method, the potential was set at 0.8 V, the sensitivity was 0.001 A/V, and the time was about 200 seconds. As shown in FIG. 1, a schematic diagram shows the PANI film prepared by the present example is disclosed.

3. Using the PANI Film As a Carrier Test Phosphate Adsorption and Release at Different Phosphate Concentrations A potential of 0.3 V was applied to the PANI film to cover phosphates on the PANI film. If the concentration of phosphate increases, the PANI film adsorbed more phosphates. By applying various negative potentials, phosphates were removed from the PANI film. The phosphate adsorption and release were tested at three phosphate concentrations of 5 µM, 500 nM, and 5 nM.

Figure 2:
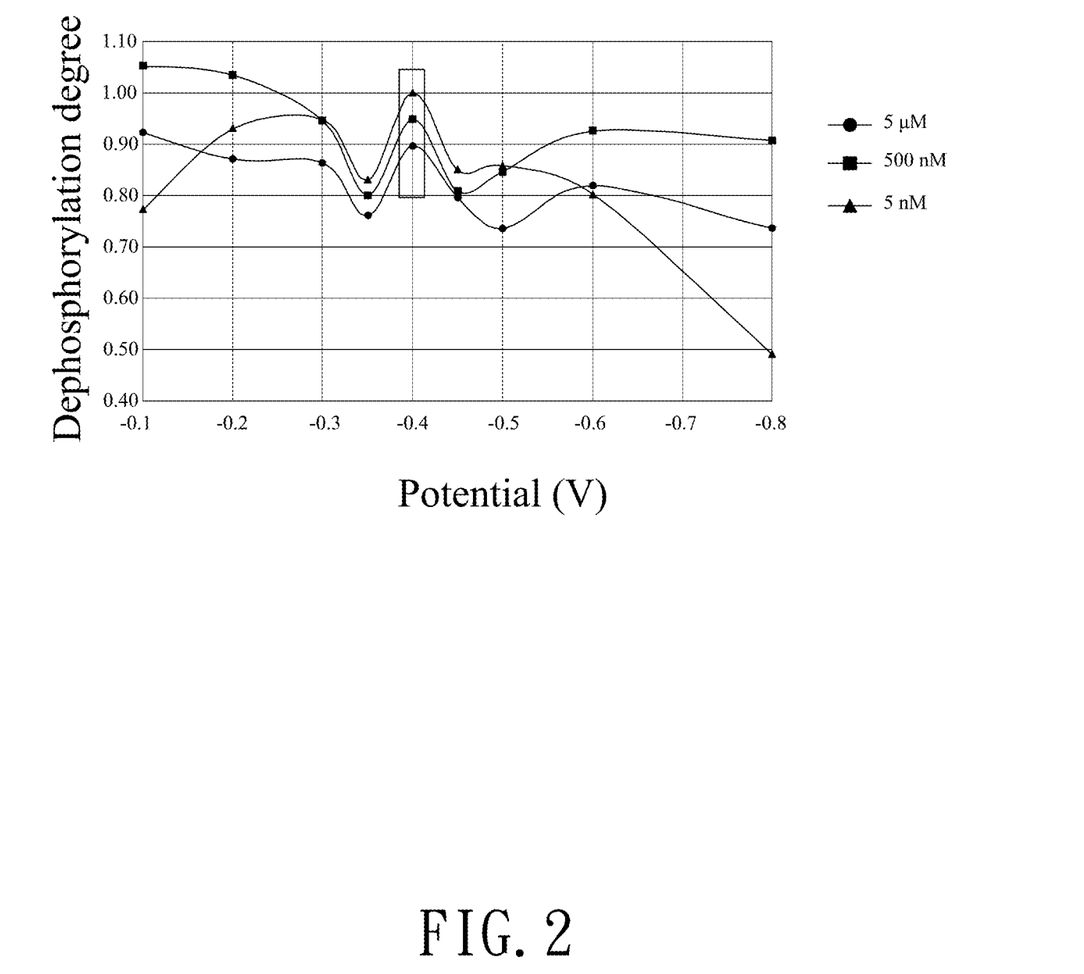
FIG. 2 shows effects of different concentrations of the phosphoric acid solution and different negative potentials on dephosphorylation degree.

Referring to FIG. 2, the results showed that the PANI film had different degrees of dephosphorylation at different concentrations of phosphoric acid solution in the different negative potentials. The preferred dephosphorylation potential was −0.4 V. The phosphate elimination rate (dephosphorylation degree) of the PANI film at 5 nM phosphate and potential of −0.4 V reached 100%.

Example 2

In order to simulate the actual status of hyper-phosphorylated Tau protein (purchased from Abcam, ab 84700) in humans, whether the phosphates could be removed from Tau proteins by the potentiostatic method was evaluated.

The PANI film was prepared by the potentiostatic method at a constant potential of 0.8 V and a frequency of −3200 Hz, and the rate at which the Tau proteins detached from the PANI film under different potentials was observed.

According to Table 1, after 10 ng/mL Tau proteins (dissolved in 0.1 M PBS buffer solution at pH 7.4) were deposited on the PANI film at 4° C. for 4 hours, the mass converted from the frequency was 770.5 ng. Then, a negative potential of −0.4 V was applied to the PANI film for 10 seconds, and the rate at which Tau proteins detached from the PANI film was evaluated. The detached proteins were measured to be 362 Hz, so the amount of proteins remaining on the PANI film were about 285.42 ng. In addition, the application of a negative potential was stopped to assess whether the Tau proteins were reabsorbed by the positively charged PANI film. After 3 minutes, the frequency was detected to decrease to −60 Hz, and the Tau protein content on the PANI film was increased to 365.82 ng. Finally, a negative potential of −0.4 V was applied to the PANI film for 20 seconds, and the Tau proteins on the PANI film were completely detached from the film. Since parts of the components on the PANI film are detached together with the Tau proteins, the mass of the PANI film became a negative value. From the result, it is known that Tau protein release rate was 26.379 Hz/s, which was very fast.

TABLE 1

| Potential (V) | Time (s) | Delta frequency (Hz) | Delta Mass (ng) |
|---|---|---|---|
| 0 | 14000 | −575 | 770.5 |
| −0.4 | 10 | 362 | 285.42 |
| 0 | 180 | −60 | 365.82 |
| −0.4 | 20 | 429.37 | −209.54 |

In order to use a scanning electron microscope (SEM) (JSM-7401F) to observe the phosphorylation of Tau proteins on the PANI film at the negative potential of −0.4 V, 2.5% glutaraldehyde was used as a protein fixing agent for fixation of Tau proteins at a temperature of 4° C. for 1-2 hours, and then proteins were rinsed with a 0.1 M PBS buffer solution (pH 7.4). Next, the fixed Tau proteins were sequentially and respectively placed in 60%, 75%, 85%, 95%, 100% alcohol for 5 minutes for dehydration. After the dehydration procedure, Tau proteins were placed in an oven, and a gold electrode attached with a sample to be tested was adhered to a copper sheet and placed in a vacuum pump to evacuate. The SEM equipment was equipped with an energy dispersive spectrometer (EDS) for simultaneously qualitative and semi-quantitative analysis of the elemental material of the micro-zone of the sample.

Figure 3:
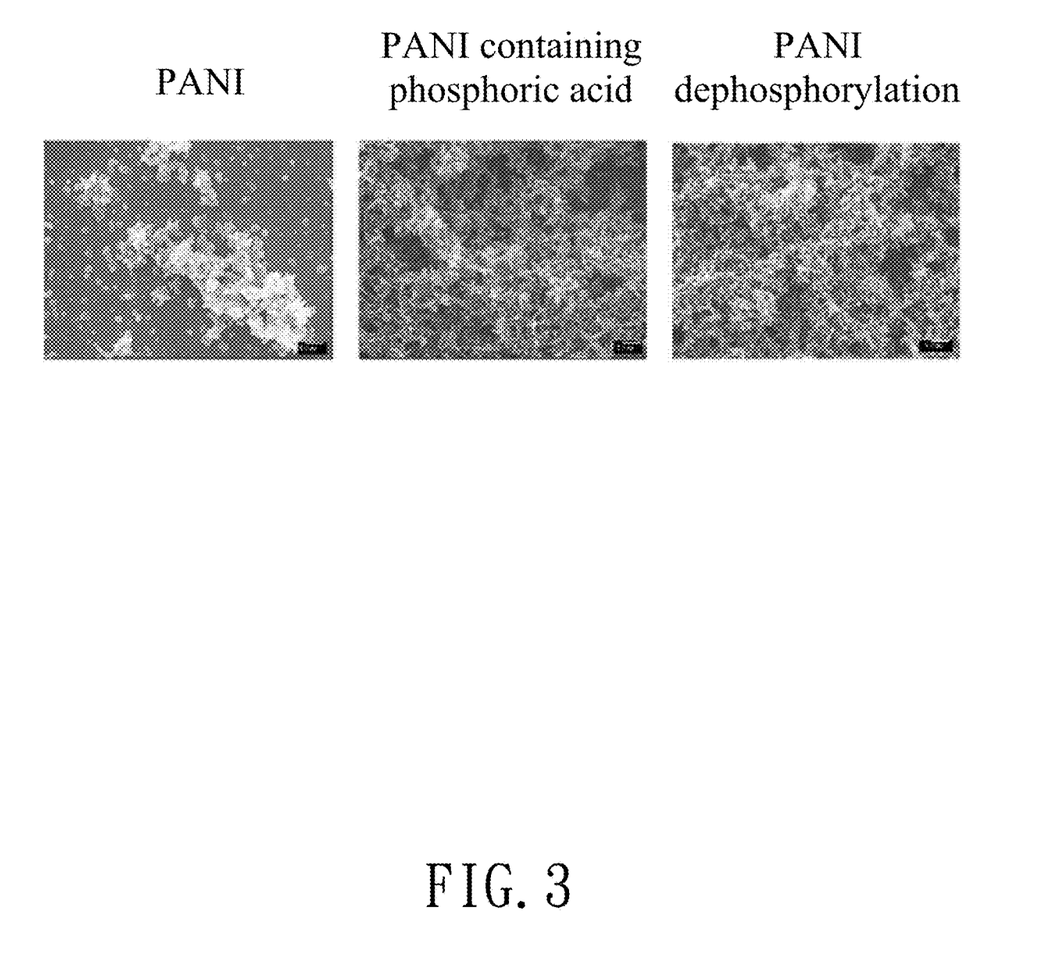
FIG. 3 is a scanning electron micrograph showing proteins on a PANI film at 7,500× magnification.
Figure 5:
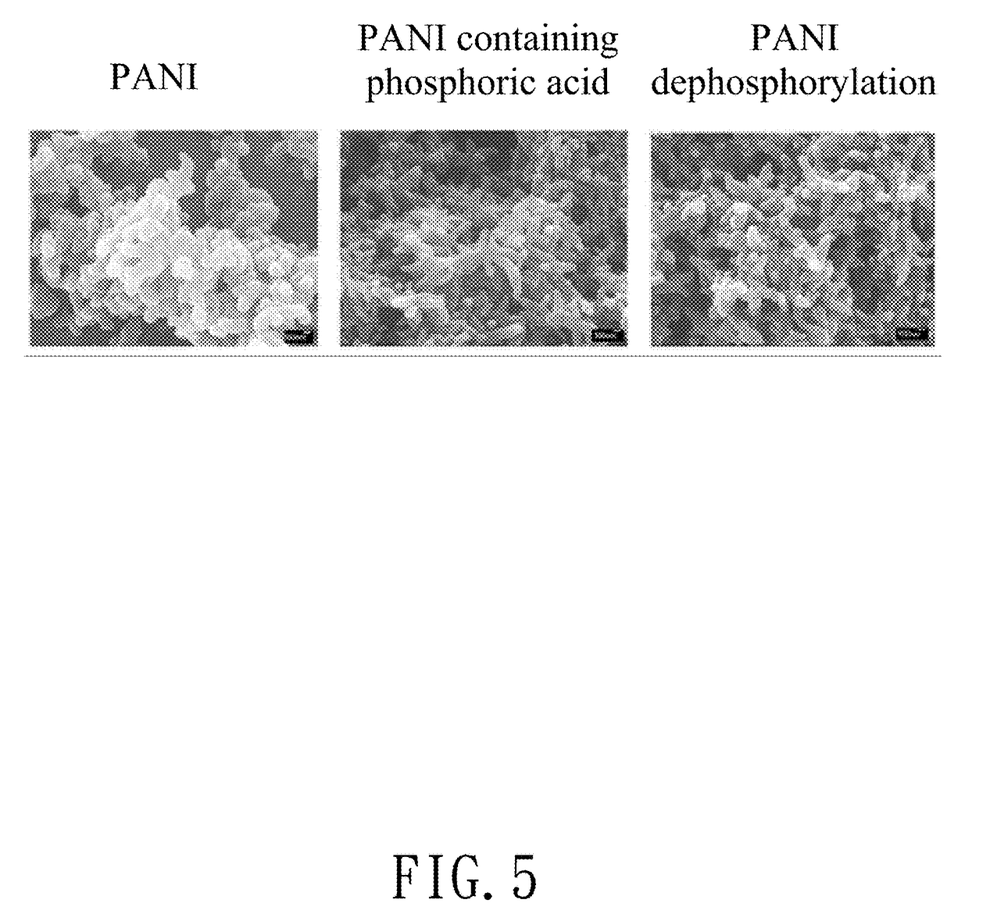
FIG. 5 is a scanning electron micrograph showing proteins on a PANI film at 30,000× magnification.

Referring to FIG. 3 and FIG. 5, two scanning electron micrographs showing phosphoric acid adsorbed or detached from the PANI films on QCM at 7,500× and 30,000× magnifications are respectively disclosed. The PANI film was shown as a fibrous network with many small branches. The phosphate concentration in this example was 0.5 µM. From the results, the main difference between the "PANI containing phosphoric acid group" and the "PANI dephosphorylation group" was that the size of the small dots on the small branches was slightly different. Compared with the "PANI dephosphorylation group" that had holes and similar structure to the original PANI film, the structure of the PANI film of the "PANI containing phosphoric acid group" was more compact.

Figure 4:
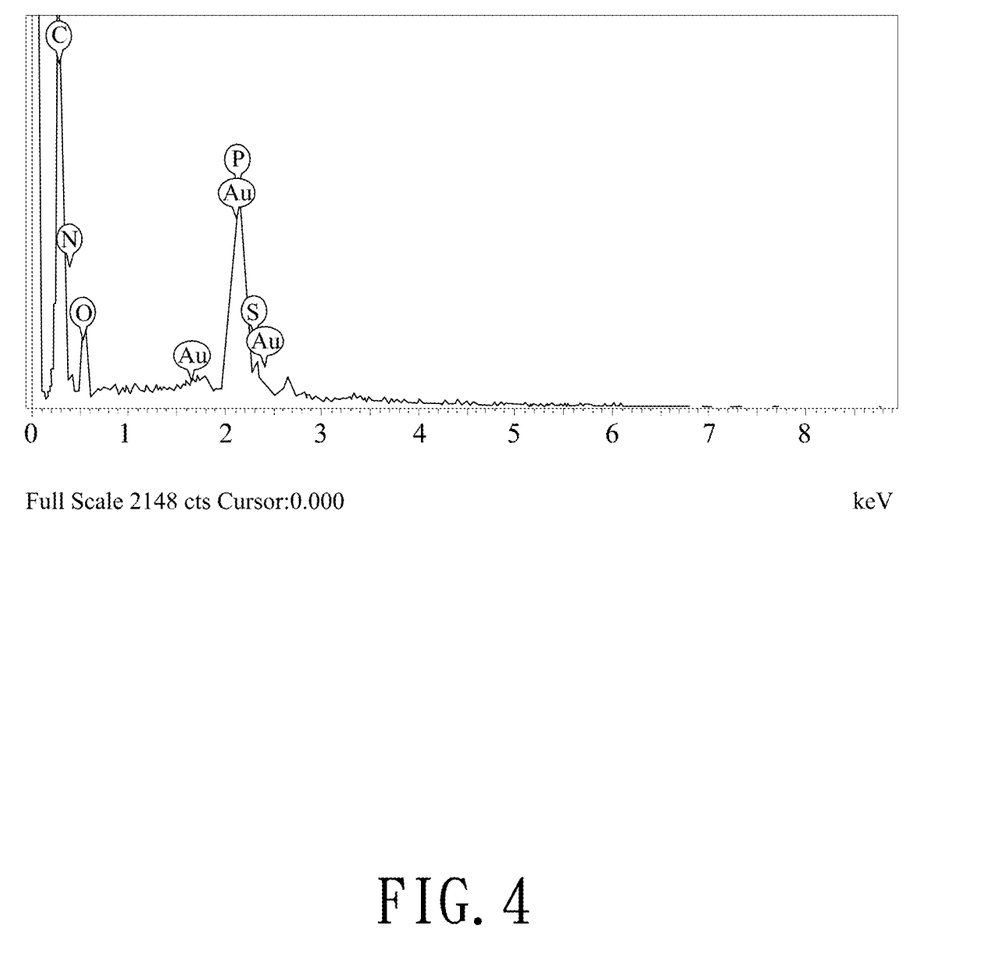
FIG. 4 shows an energy-dispersive X-ray spectroscopy of a PANI film containing phosphoric acids.
Figure 6:
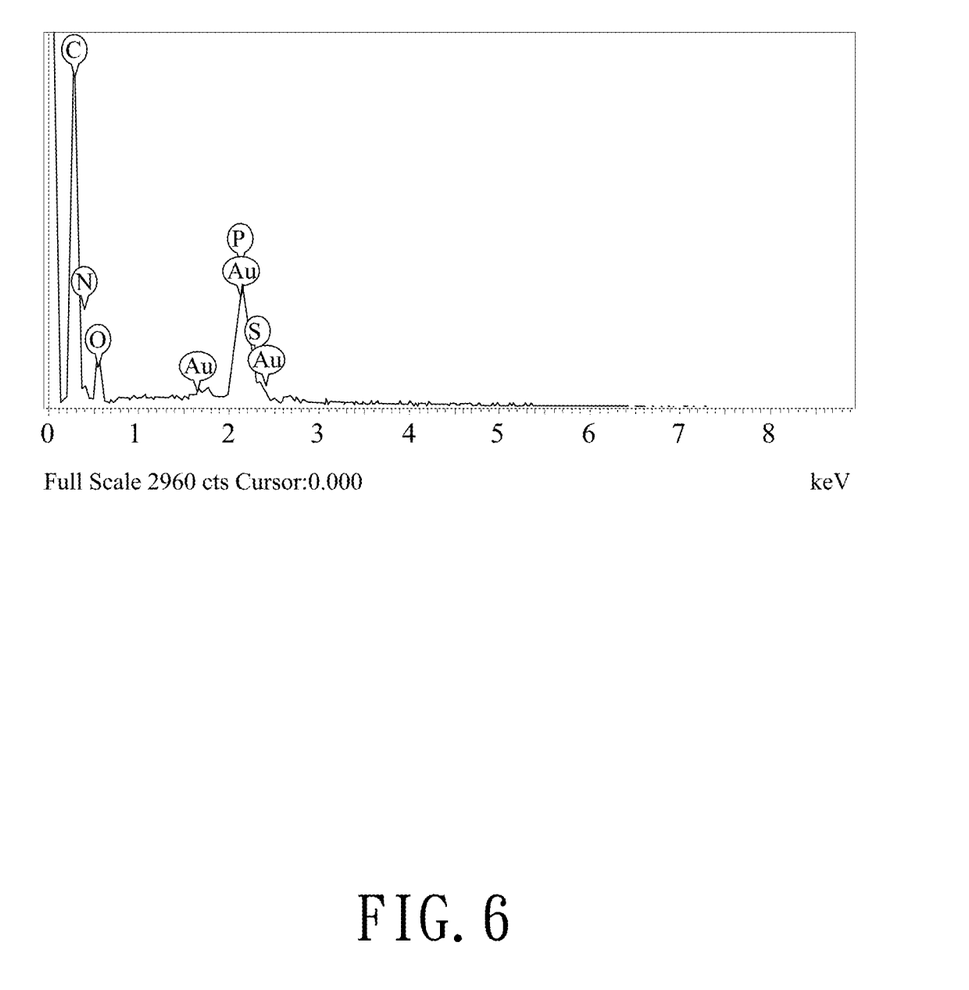
FIG. 6 shows an energy-dispersive X-ray spectroscopy of a PANI film with dephosphorylation.

Additionally, the results of qualitative and semi-quantitative analysis of the elemental material of the micro-zone of the sample conducted by the EDS method are disclosed in FIG. 4 (containing phosphoric acid), FIG. 6 (dephosphorylation) and Table 2. The nitrogen (N) element was naturally existed in the aniline itself, and the sulfur (S) element was the substance required for the conductive PANI film after doping with an acid solution. After a negative potential of −0.4 V was applied to the PANI film for dephosphorylation, the phosphorus (P) content decreased as shown in FIG. 6.

TABLE 2

| Element | Phosphorylation | | Dephosphorylation | |
|---|---|---|---|---|
| | Weight (%) | Atomic (%) | Weight (%) | Atomic (%) |
| C K | 50.92 | 81.10 | 52.85 | 83.53 |
| N K | 0.74 | 1.01 | 0.46 | 0.62 |
| O K | 9.51 | 11.37 | 8.69 | 10.31 |
| P K | 2.12 | 1.31 | 1.05 | 0.64 |
| S K | 3.29 | 1.97 | 2.70 | 1.60 |
| Au K | 33.42 | 3.25 | 34.26 | 3.30 |

Example 3

In this example, 10 ng/mL Tau proteins (dissolved in 0.1 M PBS buffer solution at pH 7.4) were deposited on the PANI film at 4° C. for 4 and 24 hours, respectively, to analyze the structure changes of the PANI film in the surface after adsorbed Tau protein at different times.

Figure 7:
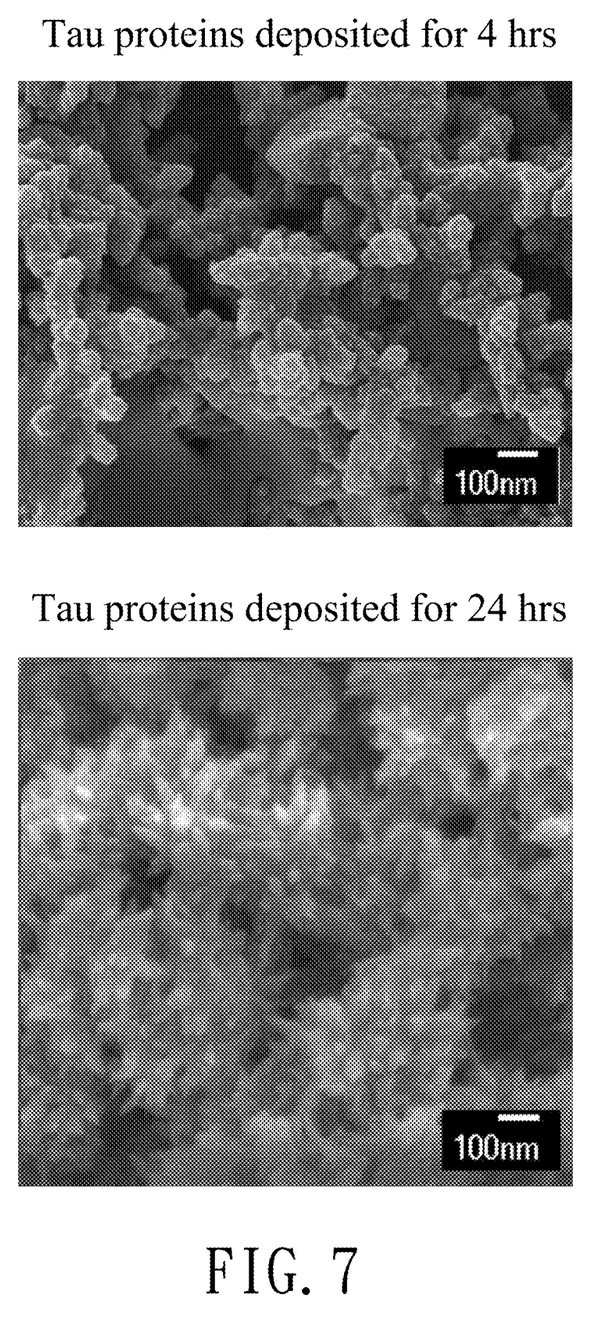
FIG. 7 is a scanning electron micrograph showing the deposition of Tau proteins on a PANI film for 4 hours and 24 hours at 45,000× magnification.

Referring to FIG. 7, a scanning electron micrograph showing the deposition of Tau proteins on a PANI film for 4 hours and 24 hours at 45,000× magnification is disclosed. The results showed that different deposition times lead to a large difference in surface structures of the PANI films. After 4 hours of deposition, the protein spheres were still coated on the PANI network and clearly visible on the bottom layer of the PANI film. After 24 hours of deposition, the network structure of the PANI film reduced protein accumulation, but the network structure was completely attached to the PANI film, and the particles on the PANI film indicated that the protein spheres were closely connected. Therefore, the preferably deposition time was 4 hours.

In order to analyze the accumulations of Tau proteins before and after phosphorylation by SEM, 2 μl of 1 ng/mL GSK-3β (Merck, product number 361524) and 1 μl of 91 μM adenosine triphosphate (ATP) (SIGMA A26209) were added to 1000 μl of PBS buffer solution to form a mixed solution. Then, the mixed solution was added to a PANI film on which the Tau protein was deposited, and the protease was added for reaction at a temperature of 30° C. to phosphorylate the Tau protein. Furthermore, a negative potential of −0.4 V was applied to the PANI film, and the accumulation of Tau proteins on the PANI film was observed and compared with the phosphorylated protein.

Figure 8:
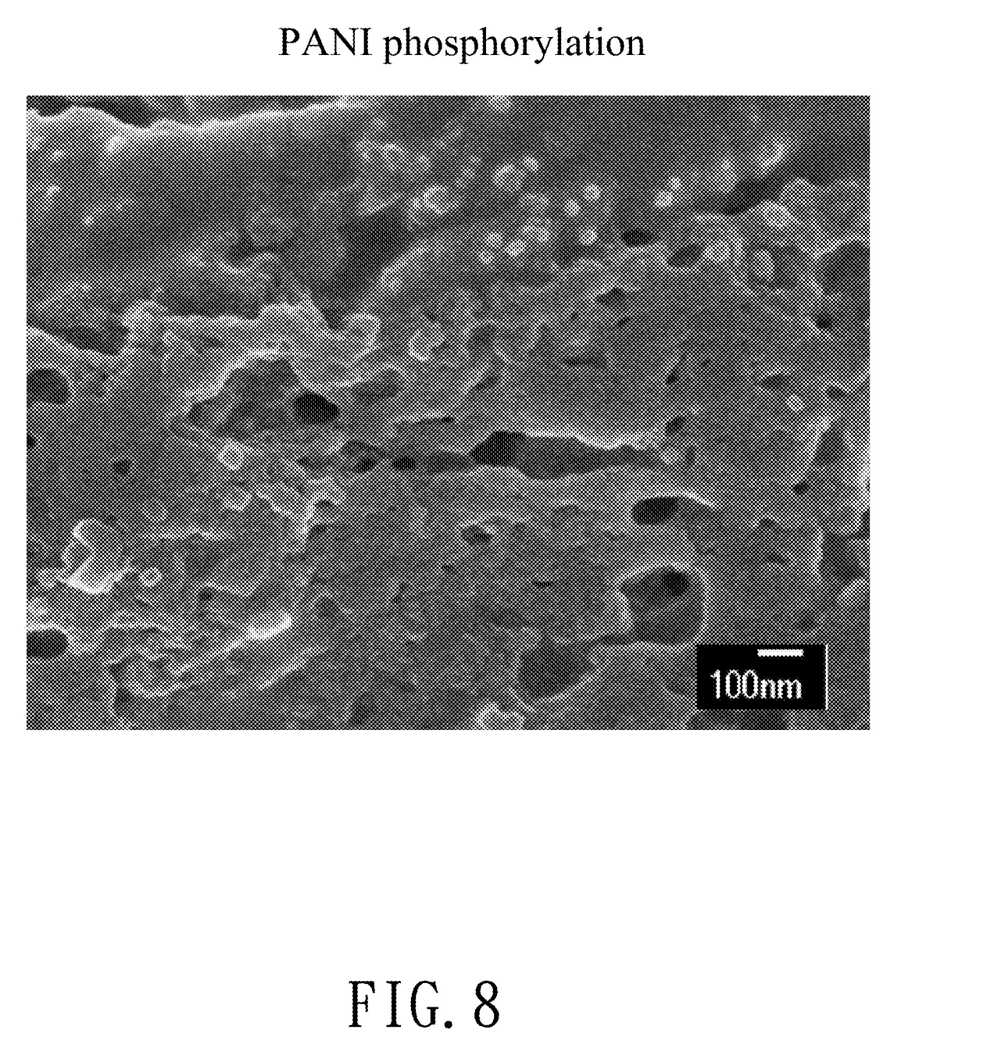
FIG. 8 is a scanning electron micrograph showing the accumulation of Tau proteins on a PANI film after phosphorylation at 45,000× magnification.

Referring to FIG. 8, the result showed that the phosphorylated Tau proteins had structural deformation and aggregation and covered the entire PANI film. The phosphorylated Tau proteins with many branches (phosphoric acid) were anchored to the bottom layer of the PANI film.

Figure 9:
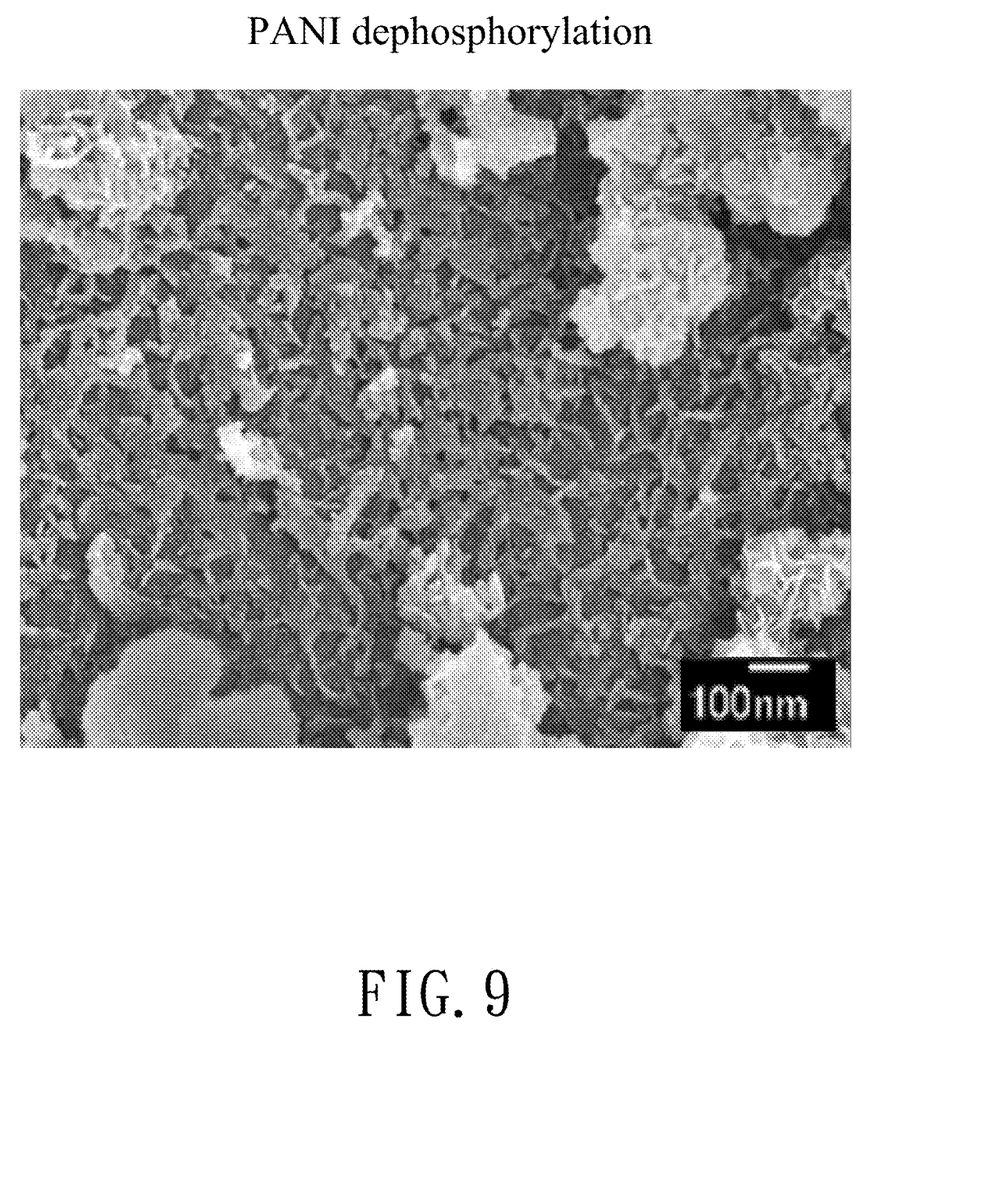
FIG. 9 is a scanning electron micrograph showing the accumulation of Tau proteins on a PANI film after dephosphorylation at 45,000× magnification.

Referring to FIG. 9, a scanning electron micrograph showing the accumulation of Tau proteins on a PANI film after dephosphorylation at 45,000× magnification is disclosed. Applying a negative potential caused ATPs to detach from the PANI film. Generally, phosphoric acids attached to the PANI film exhibit small spheres rather than flaky structures. In FIG. 9, the result showed that the PANI film had flaky and wrinkled dehydrated proteins. In addition, some of the phosphoric acids remained on a layer of crystals, and the underlying PANI film was still clearly visible.

The results of the qualitative and semi-quantitative analysis of the elemental material of the sample to be tested using the EDS method are shown in Table 3. Phosphoric acid content was significantly reduced by dephosphorylation by EDS, which indicates that ATPs and some Tau proteins can be released by applying a negative potential of −0.4 V.

TABLE 3

| Element | Phosphorylation | | Dephosphorylation | |
|---|---|---|---|---|
| | Weight (%) | Atomic (%) | Weight (%) | Atomic (%) |
| P K | 36.62 | 62.59 | 9.72 | 27.16 |
| S K | 14.75 | 24.35 | 14.70 | 39.65 |
| Au K | 48.63 | 13.07 | 75.58 | 33.19 |

Compared with the technique available now, the present invention achieves the purpose of dephosphorylated Tau proteins by electrode treatment. In practical applications, the electrode can be placed in the vicinity of the hippocampus which is particularly severely atrophic to remove the phosphates of the phosphorylated Tau protein by a specific negative potential and reduce neurofibrillary tangles and neuritic plaques caused by the accumulation of phosphorylated Tau proteins. The present invention also avoids the persistent hyper-phosphorylation of the Tau protein and thus achieves the therapeutic effect of Alzheimer's disease.

What is claimed is:

1. A method for treating Alzheimer's disease comprising:
   forming an electrochemical dephosphorylation electrode consisting of a gold electrode member having a planar contour;
   applying said electrochemical dephosphorylation electrode to a region of a patient corresponding to the patient's hippocampus, wherein the hippocampus has neurofibrillary tangles and neuritic plaques, and
   charging a surface of said gold electrode member with a negative potential in a range between −0.2V and −0.6V and applying said negative potential for a predetermined time to the patient's hippocampus, thereby dephosphorylating Tau proteins aggregated in the hippocampus as a treatment of Alzheimer's disease.

* * * * *